United States Patent [19]

Drabek et al.

[11] Patent Number: 4,908,383
[45] Date of Patent: Mar. 13, 1990

[54] N-PHENYL-N-CARBOXYTHIOUREAS AND THEIR USE IN THE CONTROL OF PESTS

[75] Inventors: Jozef Drabek, Oberwil; Josef Ehrenfreund, Allschwil, both of Switzerland

[73] Assignee: Ciba-Geigy Corporation, Ardsley, N.Y.

[21] Appl. No.: 356,665

[22] Filed: May 23, 1989

Related U.S. Application Data

[63] Continuation of Ser. No. 130,246, Dec. 8, 1987, abandoned.

[30] Foreign Application Priority Data

Dec. 17, 1986 [CH] Switzerland .................. 5056/86
Jul. 29, 1987 [CH] Switzerland .................. 2909/87

[51] Int. Cl.$^4$ .................... A01N 31/04; C07C 149/43; C07C 125/06
[52] U.S. Cl. .................... 514/485; 514/476; 514/478; 514/482; 560/16; 560/148
[58] Field of Search .............. 560/148, 16; 514/476, 514/478, 479, 482, 485

[56] References Cited

U.S. PATENT DOCUMENTS 4,194,008 3/1980 Enders et al. ............... 424/322

FOREIGN PATENT DOCUMENTS 3506236 8/1986 Fed. Rep. of Germany.
46-28112 8/1971 Japan ........................ 514/482
48-34217 10/1973 Japan ........................ 514/482

OTHER PUBLICATIONS

J. Chem. Soc., vol. 83, pp. 550–567 (1903).

*Primary Examiner*—Donald B. Moyer
*Assistant Examiner*—Karen E. Plue
*Attorney, Agent, or Firm*—Edward McC. Roberts

[57] ABSTRACT

Novel N-phenyl-N-carboxythioureas of the formula I

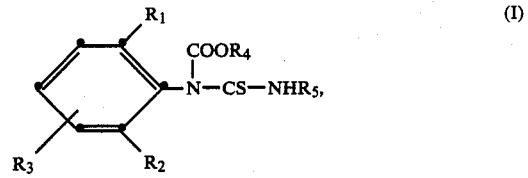

in which
$R_1$ and $R_2$ each represents $C_1$-$C_{10}$alkyl, $C_3$-$C_7$cycloalkyl or $C_5$-$C_6$cycloalkenyl,
$R_3$ represents hydrogen, halogen, $C_1$-$C_{10}$alkyl, $C_1$-$C_{10}$alkoxy or $C_1$-$C_{10}$alkylthio,
$R_4$ represents $C_1$-$C_{10}$alkyl, $C_2$-$C_{10}$alkenyl, $C_2$-$C_{10}$alkynyl or phenyl-$C_1$-$C_7$alkyl; $C_1$-$C_{10}$alkyl, $C_2$-$C_{10}$alkenyl, $C_2$-$C_{10}$alkynyl or phenyl-$C_1$-$C_7$alkyl each mono- or poly-substituted by halogen or interrupted one or several times by oxygen and/or sulphur; $C_3$-$C_8$cycloalkyl; or $C_3$-$C_8$cycloalkyl mono- or poly-substituted by halogen or by $C_1$-$C_5$alkyl, and
$R_5$ represents $C_1$-$C_{10}$alkyl; phenyl-$C_1$-$C_7$alkyl; $C_1$-$C_{10}$alkyl or phenyl-$C_1$-$C_7$alkyl each mono- or poly-substituted by halogen or interrupted one or several times by oxygen and/or sulphur; $C_3$-$C_8$cycloalkyl; or $C_3$-$C_8$cycloalkyl mono- or poly-substituted by halogen or by $C_1$-$C_5$alkyl, processes and salts of corresponding isothioureas as intermediates for their preparation, their use in pest control, and pesticidal compositions that contain at least one compound of the formula I or an active intermediate, are disclosed. The preferred field of application is the control of pests on animals and plants.

9 Claims, No Drawings

N-PHENYL-N-CARBOXYTHIOUREAS AND THEIR USE IN THE CONTROL OF PESTS

This application is a continuation of application Ser. No. 130,246, filed 12/8/87.

The present invention relates to novel substituted N-phenyl-N-carboxythioureas, to processes and intermediates for their manufacture, to pesticidal compositions that contain those compounds, and to their use in pest control.

The compounds according to the invention correspond to the formula I

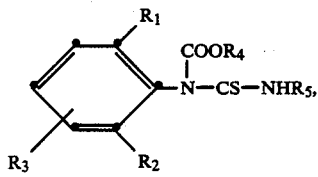

in which $R_1$ and $R_2$ each represents $C_1$-$C_{10}$alkyl, $C_3$-$C_7$cycloalkyl or $C_5$-$C_6$cycloalkenyl, $R_3$ represents hydrogen, halogen, $C_1$-$C_{10}$alkyl, $C_1$-$C_{10}$alkoxy or $C_1$-$C_{10}$alkylthio, $R_4$ represents $C_1$-$C_{10}$alkyl, $C_2$-$C_{10}$alkenyl, $C_2$-$C_{10}$alkynyl or phenyl-$C_1$-$C_7$alkyl; $C_1$-$C_{10}$alkyl, $C_2$-$C_{10}$alkenyl, $C_2$-$C_{10}$alkynyl or phenyl-$C_1$-$C_7$alkyl each mono- or poly-substituted by halogen or interrupted one or several times by oxygen and/or sulphur; $C_3$-$C_8$cycloalkyl; or $C_3$-$C_8$cycloalkyl mono- or poly-substituted by halogen or by $C_1$-$C_5$-alkyl, and $R_5$ represents $C_1$-$C_{10}$alkyl; phenyl-$C_1$-$C_7$alkyl; $C_1$-$C_{10}$alkyl or phenyl-$C_1$-$C_7$alkyl each mono- or poly-substituted by halogen or interrupted one or several times by oxygen and/or sulphur; $C_3$-$C_8$cycloalkyl; or $C_3$-$C_8$cycloalkyl mono- or poly-substituted by halogen or by $C_1$-$C_5$alkyl.

The halogens that are suitable as substituents are fluorine and chlorine as well as bromine and iodine, fluorine and chlorine being preferred.

The alkyls, alkoxy radicals and alkylthio radicals that are suitable as substituents may be straight-chained or branched. Examples of such alkyls are, inter alia: methyl, ethyl, propyl, isopropyl, butyl, i-butyl, sec.-butyl and tert.-butyl; or pentyl, hexyl and octyl and their isomers. Suitable alkoxy and alkylthio radicals are, inter alia: methoxy, methylthio, ethoxy, ethylthio, propoxy, propylthio, isopropoxy and isopropylthio; or butoxy and butylthio and their isomers.

The alkenyls and alkynyls that are suitable as substituents may be straight-chained or branched and may contain one or more unsaturated bonds. It is also possible for di- and tri-unsaturated bonds to occur in the same radical. Those unsaturated radicals advantageously contain from one to five carbon atoms. Examples of such alkenyls and alkynyls are, inter alia: vinyl, allyl, 1-propenyl, isopropenyl, allenyl, butenyls, butadienyls, hexenyls, hexanedienyl, ethynyl, 1-propynyl, 2-propynyl, butynyls, pentynyls, hexynyls, hexadiynyls and 2-penten-4-ynyl.

The phenylalkyls that are suitable as substituents may be straight-chained or branched. Suitable examples are, inter alia: benzyl, phenethyl, phenpropyl and phenisopropyl; and phenbutyl and its isomers.

If the alkyls, alkenyls, alkynyls and phenylalkyls that are suitable as substituents are substituted by halogen, they may be only partially halogenated or, alternatively, may be perhalogenated. The halogen substitution of the phenylalkyls may take place either in the phenyl nucleus or in the alkyl chain, or in both at the same time. The halogens, alkyls, alkenyls, alkynyls and phenylalkyls here have the definitions given above. Examples of such groups are, inter alia: methyl mono- to tri-substituted by fluorine, chlorine and/or bromine, such as, for example, $CHF_2$ or $CF_3$; ethyl substituted one to five times by fluorine, chlorine and/or bromine, such as, for example, $CH_2CF_3$, $CF_2CF_3$, $CF_2CCl_3$, $CF_2CHCl_2$, $CF_2CHF_2$, $CF_2CFCl_2$, $CF_2CHBr_2$, $CF_2CHClF$, $CF_2CHBrF$ or $CClFCHClF$; propyl or isopropyl each substituted one to seven times by fluorine, chlorine and/or bromine, such as, for example, $CH_2CHBrCH_2Br$, $CF_2CHFCF_3$, $CH_2CF_2CF_3$ or $CH(CF_3)_2$; butyl, or one of its isomers, substituted one to nine times by fluorine, chlorine and/or bromine, such as, for example, $CF(CF_3)CHFCF_3$ or $CH_2(CF_2)_2CF_3$; vinyl, propynyl or pentadiynyl each mono- to tri-substituted by fluorine, chlorine and/or bromine; allyl, 1-propenyl, butadienyl or a butynyl each substituted one to five times by fluorine, chlorine and/or bromine; butenyl, pentadienyl or pentynyl each substituted one to seven times by fluorine, chlorine and/or bromine; benzyl substituted one to seven times by fluorine, chlorine and/or bromine; phenethyl substituted one to nine times by fluorine, chlorine and/or bromine; and phenpropyl or phenisopropyl substituted one to eleven times by fluorine, chlorine and/or bromine.

The alkyls, alkenyls, alkynyls and phenylalkyls that are suitable as substituents and are interrupted by oxygen and/or sulphur may be both simple ethers and polyalkylene glycols or thioglycols. Chains that contain both oxygen and sulphur are also possible. Examples are, inter alia: radicals such as methoxymethyl, methylthiomethyl, methoxymethoxymethyl, methoxyethyl, ethoxyethyl, ethylthioethyl, vinyloxymethyl, allylthioethyl, methoxypropynyl, benzyloxymethyl and benzylthioethyl.

The cycloalkyls and cycloalkenyls that are suitable as substituents are, for example, cyclopropyl, cyclobutyl, cyclopentyl, 2-cyclopenten-1-yl, cyclohexyl and cyclohexenyl. Those radicals may be mono- or poly-substituted by halogen or by alkyl, such as, for example, 2-chlorocyclopropyl, 2,2-dimethylcyclopropyl, 3-chlorocyclobutyl, 2-methylcyclohexyl, 2,4-dimethylcyclohexyl and 2,4,6-trimethylcyclohexyl.

The compounds of the formula I that should be given special emphasis are those in which $R_1$ represents $C_1$-$C_5$alkyl, cyclopentyl or cyclopentenyl, $R_2$ represents $C_1$-$C_5$alkyl, or $R_1$ and $R_2$ each represents $C_1$-$C_5$alkyl, $R_3$ represents hydrogen, halogen, $C_1$-$C_3$alkyl or $C_1$-$C_3$alkoxy, $R_4$ represents $C_1$-$C_5$alkyl, $C_2$-$C_5$alkenyl or $C_2$-$C_5$alkynyl; $C_1$-$C_5$alkyl, $C_2$-$C_5$alkenyl, $C_2$-$C_5$alkynyl or phenyl-$C_1$-$C_5$alkyl each mono- or polysubstituted by halogen or interrupted by oxygen and/or sulphur; or $C_3$-$C_6$cycloalkyl, and $R_5$ represents $C_1$-$C_5$alkyl, or $C$-$C_5$alkyl mono- or poly-substituted by halogen or interrupted by oxygen and/or sulphur.

Preferred compounds of the formula I are those in which $R_1$ represents $C_1$-$C_3$alkyl or cyclopentyl, $R_2$ represents $C_1$-$C_3$alkyl,
$R_3$ represents hydrogen, and
$R_4$ and $R_5$ represent $C_1$-$C_4$alkyl.

Examples of compounds of the formula I are, inter alia:

| $R_1$ | $R_2$ | $R_3$ | $R_4$ | $R_5$ |
|---|---|---|---|---|
| $CH_3$ | $CH_3$ | H | $CH_3$ | $CH_3$ |
| $CH_3$ | $CH_3$ | 4-$CH_3$ | $CH_3$ | $CH_3$ |
| $CH_3$ | $CH_3$ | H | $CH_3$ | $C_2H_5$ |
| $CH_3$ | $CH_3$ | H | $C_2H_5$ | $C_2H_5$ |
| $CH_3$ | $CH_3$ | H | $C_2H_5$ | $CH(CH_3)_2$ |
| $CH_3$ | $CH(CH_3)_2$ | H | $CH_3$ | $CH(CH_3)_2$ |
| $CH_3$ | $C_2H_5$ | 4-$SCH_3$ | $C_2H_5$ | $(CH_2)_2(CH_3)$ |
| $C_2H_5$ | $CH_3$ | H | $CH_3$ | $CH_3$ |
| $C_2H_5$ | $CH_3$ | H | $C_2H_5$ | $C_2H_5$ |
| $C_2H_5$ | $CH_3$ | H | $CH(CH_3)_2$ | $CH(CH_3)_2$ |
| $C_2H_5$ | $C_2H_5$ | H | $CH_3$ | $CH_3$ |
| $C_2H_5$ | $C_2H_5$ | H | $C_2H_5$ | $C_2H_5$ |
| $C_2H_5$ | $C_2H_5$ | H | $CH_3$ | $CH(CH_3)_2$ |
| $C_2H_5$ | $C_2H_5$ | H | $CH_3$ | $C(CH_3)_3$ |
| $C_2H_5$ | $C_2H_5$ | H | $(CH_2)_3CH_3$ | $CH(CH_3)_2$ |
| $C_2H_5$ | $C_2H_5$ | H | $CH_2CH_2Cl$ | $CH(CH_3)_2$ |
| $C_2H_5$ | $C_2H_5$ | H | $CH_2$-$C_6H_5$ | $CH(CH_3)_2$ |
| $C_2H_5$ | $C_2H_5$ | H | $CH_3$ | cyclopentyl |
| $C_2H_5$ | $C_2H_5$ | 4-$O(CH_2)_3CH_3$ | $C_2H_5$ | $CH(CH_3)_2$ |
| $C_2H_5$ | $CH(CH_3)C_2H_5$ | H | $C_2H_5$ | $CH(CH_3)_2$ |
| $(CH_2)_2CH_3$ | $CH_3$ | H | $CH_3$ | $CH_3$ |
| $(CH_2)_2CH_3$ | $C_2H_5$ | H | $C_2H_5$ | $C_2H_5$ |
| $(CH_2)_2CH_3$ | $(CH_2)_2CH_3$ | H | $(CH_2)_2CH_3$ | $(CH_2)_2CH_3$ |
| $(CH_2)_2CH_3$ | $CH(CH_3)_2$ | H | $CH(CH_3)_2$ | $CH(CH_3)_2$ |
| $CH(CH_3)_2$ | $CH_3$ | H | $CH_3$ | $CH_3$ |
| $CH(CH_3)_2$ | $C_2H_5$ | H | $C_2H_5$ | $C_2H_5$ |
| $CH(CH_3)_2$ | $C_2H_5$ | H | $C_2H_5$ | $CH(CH_3)_2$ |
| $CH(CH_3)_2$ | $CH(CH_3)_2$ | H | $C_2H_5$ | $(CH_2)_2CH_3$ |
| $CH(CH_3)_2$ | $(CH_2)_2CH_3$ | H | $(CH_2)_2CH_3$ | $(CH_2)_2CH_3$ |
| $CH(CH_3)_2$ | $CH(CH_3)_2$ | 4-Cl | $CH_3$ | $CH_3$ |
| $CH(CH_3)_2$ | $CH(CH_3)_2$ | H | $CH_3$ | $CH_2CH(CH_3)_2$ |
| $CH(CH_3)_2$ | $CH(CH_3)_2$ | H | $C_2H_5$ | $C_2H_5$ |
| $CH(CH_3)_2$ | $CH(CH_3)_2$ | H | $(CH_2)_2CH_3$ | $(CH_2)_2CH_3$ |
| $CH(CH_3)_2$ | $CH(CH_3)_2$ | H | $CH(CH_3)_2$ | $CH(CH_3)_2$ |
| $CH(CH_3)_2$ | $CH(CH_3)_2$ | H | $(CH_2)_3CH_3$ | $CH(CH_3)_2$ |
| $CH(CH_3)_2$ | $CH(CH_3)_2$ | H | $CH_2CH(CH_3)_2$ | $CH(CH_3)_2$ |
| $CH(CH_3)_2$ | $CH(CH_3)_2$ | H | $(CH_2)_2OCH_3$ | $CH(CH_3)_2$ |
| $CH(CH_3)_2$ | $CH(CH_3)_2$ | H | $C_2H_5$ | $CH(CH_3)C_2H_5$ |
| $CH(CH_3)_2$ | $CH(CH_3)_2$ | H | $CH_2$—$C_6H_5$ | $CH(CH_3)_2$ |
| $CH(CH_3)_2$ | $CH(CH_3)_2$ | H | $(CH_2)_3CH_3$ | $CH(CH_3)_2$ |
| $CH(CH_3)_2$ | $CH(CH_3)_2$ | H | $(CH_2)_2Cl$ | $CH(CH_3)_2$ |
| $CH(CH_3)_2$ | $CH(CH_3)_2$ | H | $CH=CH_2$ | $CH(CH_3)_2$ |
| $CH(CH_3)_2$ | $CH(CH_3)_2$ | H | $(CH_2)_2CCl_3$ | $CH(CH_3)_2$ |
| $CH(CH_3)_2$ | $CH(CH_3)_2$ | H | $CH_3$ | $CH(CH_3)CH_2OCH_3$ |
| $CH(CH_3)_2$ | $CH(CH_3)_2$ | H | $CH_3$ | $CH_2C(CH_3)_2SCH_3$ |
| $CH(CH_3)_2$ | $CH(CH_3)_2$ | H | $C(CH_3)_3$ | $CH(CH_3)_2$ |
| $CH(CH_3)_2$ | $CH(CH_3)_2$ | 4-Br | $CH_3$ | $CH(CH_3)_2$ |
| $CH(CH_3)_2$ | $CH(CH_3)_2$ | 4-Br | $C_2H_5$ | $CH(CH_3)_2$ |
| $CH(CH_3)_2$ | $CH(CH_3)_2$ | 4-$OCH_3$ | $CH_3$ | $CH(CH_3)_2$ |
| $C_2H_5$ | $CH(CH_3)_2$ | 4-$OC_2H_5$ | $CH_3$ | $CH(CH_3)_2$ |
| $C_2H_5$ | $CH(CH_3)_2$ | 4-$OC_2H_5$ | $C_2H_5$ | $CH(CH_3)_2$ |
| $C_2H_5$ | $CH(CH_3)_2$ | 4-$CH_3$ | $CH_3$ | $CH(CH_3)_2$ |
| $C_2H_5$ | $CH(CH_3)_2$ | 4-$CH_3$ | $C_2H_5$ | $CH(CH_3)_2$ |
| $CH(CH_3)_2$ | $CH(CH_3)_2$ | 4-$CH_3$ | $CH_3$ | $CH(CH_3)_2$ |
| $CH(CH_3)_2$ | $CH(CH_3)_2$ | 4-$CH_3$ | $C_2H_5$ | $CH(CH_3)_2$ |
| $CH(CH_3)_2$ | $CH(CH_3)_2$ | 4-$C_2H_5$ | $CH_3$ | $CH(CH_3)_2$ |
| $CH(CH_3)_2$ | $CH(CH_3)_2$ | 4-$C_2H_5$ | $C_2H_5$ | $CH(CH_3)_2$ |
| $CH(CH_3)_2$ | $CH(CH_3)_2$ | 4-$CH(CH_3)_2$ | $CH_3$ | $CH(CH_3)_2$ |
| $CH(CH_3)_2$ | $CH(CH_3)_2$ | 4-$CH(CH_3)_2$ | $C_2H_5$ | $CH(CH_3)_2$ |

The compounds of the formula I according to the invention can be prepared by methods that are known in principle, for example as follows:

(a) a thiourea of the formula II

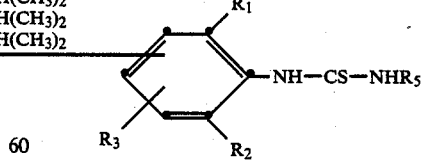

(II)

is reacted with a haloformic acid ester of the formula III

 (III)

in a solvent and in the presence of a base, under normal pressure and at from $-30°$ to $+100°$ C., or (b) a salt of an isothiourea of the formula IV

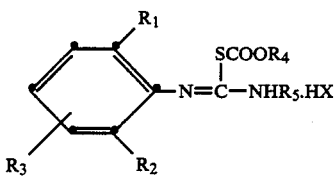

is hydrolysed at room temperature in an aqueous solution. In formulae II to IV, $R_1$, $R_2$, $R_3$, $R_4$ and $R_5$ have the meanings given for formula I and X represents the radical of a hydrohalic acid, especially chlorine.

Suitable solvents are solvents and diluents that are inert towards the reactants, such as, for example, ethers and ethereal compounds, such as, inter alia, diethyl ether, diisopropyl ether, dioxan or tetrahydrofuran; aromatic hydrocarbons, such as benzene, toluene or xylenes; ketones, such as acetone, methyl ethyl ketone or cyclohexanone; nitriles, such as acetonitrile; or halogenated hydrocarbons, such as chloroform or methylene chloride.

Suitable bases may be of organic or inorganic origin, such as, for example, sodium hydride, sodium or calcium carbonate, tertiary amines, such as triethylamine, triethylenediamine or 4-dimethylaminopyridine, or pyridine.

The thioureas of the formula II for their part can be prepared by processes that are known in principle, for example by reacting an isothiocyanate of the formula V

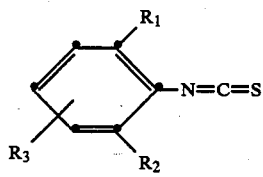

with an amine of the formula VI

   (VI)

$R_1$, $R_2$, $R_3$ and $R_5$ in the formulae V and VI having the meanings given for formula I.

The process for the preparation of the compounds of the formula II is advantageously carried out in the presence of a solvent or diluent that is inert towards the reactants, at a reaction temperature of from 0° to +100° C. and under normal pressure. Examples of suitable solvents and diluents have already been given for the process for the preparation of the compounds of the formula I.

The salts of the isothioureas of the formula IV can be prepared by processes that are known in principle, for example by reacting a thiourea of the formula II with a haloformic acid ester of the formula III in a solvent under normal pressure and at a temperature of from −20° to +100° C. The reaction with chloroformic acid ester is especially preferred.

The compounds of the formula IV are novel and the present invention relates also to these compounds. The compounds of the formulae II, III, V and VI, on the other hand, are known and can be prepared by processes that are known in principle.

Surprisingly, it has been found that the compounds of the formula I according to the invention and the intermediates of the formula IV are valuable active ingredients in pest control, while being well tolerated by warm-blooded animals, fish and plants. The compounds of the formulae I and IV are suitable, for example, for controlling pests on animals and plants. Such pests belong mainly to the arthropod family, such as, especially, insects of the orders Lepidoptera, Coleoptera, Homoptera, Heteroptera, Diptera, Thysanoptera, Orthoptera, Anoplura, Siphonaptera, Mallophaga, Thysanura, Isoptera, Psocoptera or Hymenoptera, and arachnids of the order Acarina, such as, for example, mites and ticks. It is possible to control every stage of development of the pests, that is to say adults, pupae and nymphs and also, especially, larvae and eggs. For example, larvae and eggs of harmful phytopathogenic insects and mites can be controlled effectively in ornamental crops and crops of useful plants, such as, for example, in fruit and vegetable crops, and sucking insects, such as, for example, rice cicadas and aphids, and soil insects, such as, for example, species of Diabrotica, can be controlled effectively in corn crops. If compounds of the formulae I and IV are ingested by imagines, their action may manifest itself in the immediate death of the pests or in the production of fewer eggs and/or in a reduced rate of emergence. The latter phenomenon can be observed especially in the case of Coleoptera. Animal-parasitic pests to be controlled, especially on pets and useful animals, are especially ectoparasites, such as, for example, mites and ticks, and Diptera, such as, for example, *Lucilia sericata*. In addition, the compounds of the formula I and their intermediates of the formula IV exhibit a marked microbicidal action. Long-lasting control especially of plant-pathogenic fungi of the class Oomycetidae, such as, for example, families of the order Peronosporales (Plasmopara sp.), is possible.

The good pesticidal action of the compounds of the formula I and IV according to the invention corresponds to a mortality of at least from 50 to 60% of the pests mentioned.

The action of the compounds according to the invention or of the compositions containing them can be broadened considerably and adapted to given conditions by the addition of other insecticides and/or acaricides. Suitable additives are, for example, representatives of the following classes of active ingredient: organic phosphorus compounds, nitrophenols and derivatives thereof, formamidines, ureas, carbamates, pyrethroids, chlorinated hydrocarbons and *Bacillus thuringiensis* preparations.

The compounds of the formulae I and IV are used in unmodified form or, preferably, together with the adjuvants customary in the art of formulation and they can therefore be processed in known manner, for example, into emulsifiable concentrates, directly sprayable or dilutable solutions, dilute emulsions, wettable powders, soluble powders, dusts, granulates, and encapsulations in, for example, polymeric sustances. As with the compositions, the methods of application, such as spraying, atomising, dusting, scattering and pouring, are chosen in accordance with the intended objectives and the prevailing circumstances.

The formulations, i.e. the compositions or preparations containing the active ingredient of the formula I and/or IV or combinations of those active ingredients with other insecticides or acaricides, and, where appropriate, a solid or liquid adjuvant, are prepared in known manner, for example by intimately mixing and/or grinding the active ingredients with extenders, such as, for example, solvents, solid carriers and, where appropriate, surface-active compounds (surfactants).

Suitable solvents are: aromatic hydrocarbons, preferably the fractions $C_8$ to $C_{12}$, such as, for example, xylene mixtures or substituted naphthalenes, phthalic acid esters, such as dibutyl or dioctyl phthalate, aliphatic hydrocarbons, such as cyclohexane or paraffins, alcohols and glycols and their ethers and esters, such as ethanol, ethylene glycol, ethylene glycol monomethyl or monoethyl ether, ketones, such as cyclohexanone, strongly polar solvents, such as N-methyl-2-pyrrolidone, dimethyl sulphoxide or dimethylformamide, and also optionally epoxidised vegetable oils, such as epoxidised coconut oil or soybean oil, or water.

The solid carriers used, for example for dusts and dispersible powders, are generally natural mineral fillers, such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, such as, for example, pumice, broken brick, sepiolite or bentonite, and suitable nonsorbent carriers are, for example, calcite or sand. In addition, it is possible to use a large number of granulated materials of inorganic or organic nature, such as, especially, dolomite or pulverised plant residues.

Depending on the nature of the active ingredient of the formula I or IV to be formulated or of the combinations of those active ingredients with other insecticides or acaricides, suitable surface-active compounds are nonionic, cationic and/or anionic surfactants having good emulsifying, dispersing and wetting properties. The term "surfactants" should also be understood as meaning mixtures of surfactants.

Suitable anionic surfactants may be both so-called water-soluble soaps and water-soluble synthetic surface-active compounds.

Suitable soaps are the alkali metal salts, alkaline earth metal salts and unsubstituted or substituted ammonium salts of higher fatty acids ($C_{10}$-$C_{22}$), such as, for example, the sodium or potassium salts of oleic or stearic acid, or of natural fatty acid mixtures, which can be obtained, for example, from coconut or tallow oil. As surfactants there should also be mentioned fatty acid methyltaurine salts and modified and unmodified phospholipids.

So-called synthetic surfactants are, however, more often used, especially fatty sulphonates, fatty sulphates, sulphonated benzimidazole derivatives or alkylarylsulphonates.

The fatty sulphonates and fatty sulphates are generally in the form of alkali metal salts, alkaline earth metal salts or unsubstituted or substituted ammonium salts and generally have an alkyl radical having from 8 to 22 carbon atoms, alkyl also including the alkyl moiety of acyl radicals, for example the sodium or calcium salt of lignosulphonic acid, of dodecylsulphuric acid ester or of a fatty alcohol sulphate mixture produced from natural fatty acids. These also include the salts of sulphuric acid esters and sulphonic acids of fatty alcohol/ethylene oxide adducts. The sulphonated benzimidazole derivatives contain preferably 2 sulphonic acid groups and one fatty acid radical having approximately from 8 to 22 carbon atoms. Alkylarylsulphonates are, for example, the sodium, calcium or triethanolamine salts of dodecylbenzenesulphonic acid, of dibutylnaphthalenesulphonic acid or of a naphthalenesulphonic acid/formaldehyde condensation product. Also suitable are corresponding phosphates, such as, for example, salts of the phosphoric acid ester of an adduct of p-nonylphenol with from 4 to 14 mols of ethylene oxide.

Suitable nonionic surfactants are especially polyglycol ether derivatives of aliphatic or cycloaliphatic alcohols, of saturated or unsaturated fatty acids and of alkylphenols, that may contain from 3 to 30 glycol ether groups and from 8 to 20 carbon atoms in the (aliphatic) hydrocarbon radical and from 6 to 18 carbon atoms in the alkyl radical of the alkylphenols. Further suitable nonionic surfactants are the water-soluble adducts of polyethylene oxide with polypropylene glycol, ethylenediaminopolypropylene glycol and alkylpolypropylene glycol containing from 1 to 10 carbon atoms in the alkyl chain, which adducts contain from 20 to 250 ethylene glycol ether groups and from 10 to 100 propylene glycol ether groups. The said compounds normally contain from 1 to 5 ethylene glycol units per propylene glycol unit.

There may be mentioned as examples of nonionic surfactants nonylphenolpolyethoxyethanols, castor oil polyglycol ethers, castor oil thioxilate, polypropylene-/polyethylene oxide adducts, tributylphenoxypolyethoxyethanol, polyethylene glycol and octylphenoxypolyethoxyethanol. Also suitable are fatty acid esters of polyoxyethylenesorbitan, such as polyoxyethylenesorbitan trioleate.

Cationic surfactants are especially quaternary ammonium salts that contain, as N-substituent, at least one alkyl radical having from 8 to 22 carbon atoms and, as further substituents, lower optionally halogenated alkyl, benzyl or lower hydroxyalkyl radicals. The salts are preferably in the form of halides, methyl sulphates or ethyl sulphates, for example stearyltrimethylammonium chloride or benzyldi(2-chloroethyl)ethylammonium bromide.

The surfactants customarily employed in the art of formulation are described, inter alia, in the following publications: "McCutcheon's Detergents and Emulsifiers Annual" MC Publishing Corp., Ridgewood, N.J., 1979; Dr. Helmut Stache, "Tensid-Taschenbuch", Carl Hanser Verlag, Munich/Vienna 1981.

The pesticidal preparations generally contain from 0.1 to 99%, especially from 0.1 to 95%, active ingredient of the formula I or IV or combinations of those active ingredients with other insecticides or acaricides, from 1 to 99.9% solid or liquid adjuvant and from 0 to 25%, especially from 0.1 to 20%, surfactant. Whereas commercial products will preferably be formulated as concentrates, the end user will normally employ dilute formulations, which contain considerably lower concentrations of active ingredient.

The compositions may also contain other adjuvants, such as stabilisers, anti-foams, viscosity regulators, binders, tackifiers and fertilisers, or other active ingredients for achieving special effects.

EXAMPLE 1: PREPARATION 1.1. Intermediates 1.1.1.
N-(2,6-diisopropylphenyl)-N'-sec.-butyl-S-methoxycarbonylisothiourea hydrochloride 8.8 g of N-(2,6-diisopropylphenyl)-N'-sec.-butylthiourea are dissolved in 50 ml of acetone, and 3.78 g of chloroformic acid methyl ester are added thereto while stirring. The reaction mixture is stirred for a further 3 hours and then left to stand at room temperature for 10 hours. The product which crystallises out is filtered off with suction and dried. The title compound of the formula

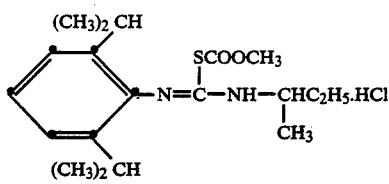 (Verb. 1.1.1.)

is obtained in the form of colourless crystals; m.p. 136°–138° C. with decomposition.

The following compounds are prepared in analogous manner:

solved in 250 ml of ethanol, and 40 ml of water are added thereto. The reaction mixture is left to stand at room temperature for 12 hours. The resulting crystals are then filtered off with suction and dried. The title compound of the formula

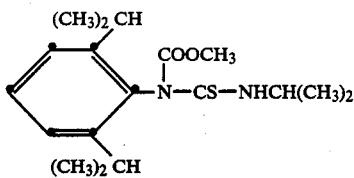 (Cpd. 1.2.1.)

is obtained in the form of colourless crystals; m.p. 98°–99° C.

The following compounds are prepared in analogous manner:

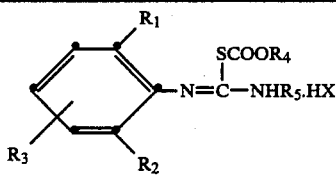

| Comp. No. | $R_1$ | $R_2$ | $R_3$ | $R_4$ | $R_5$ | X | M.p. °C. |
|---|---|---|---|---|---|---|---|
| 1.1.2. | $CH_3$ | $i-C_3H_7$ | H | $CH_3$ | $i-C_3H_7$ | Cl | 120 with decomp. |
| 1.1.3. | $C_2H_5$ | $i-C_3H_7$ | H | $CH_3$ | $i-C_3H_7$ | Cl | 124 with decomp. |
| 1.1.4. | $C_2H_5$ | $i-C_3H_7$ | H | $C_2H_5$ | $i-C_3H_7$ | Cl | 129 with decomp. |
| 1.1.5. | $C_2H_5$ | $i-C_3H_7$ | H | $i-C_4H_9$ | $i-C_3H_7$ | Cl | 102–103 |
| 1.1.6. | $i-C_3H_7$ | $i-C_3H_7$ | H | $CH_3$ | $i-C_3H_7$ | Cl | 130 with decomp. |
| 1.1.7. | $i-C_3H_7$ | $i-C_3H_7$ | H | $C_2H_5$ | $i-C_3H_5$ | Cl | 141 with decomp. |
| 1.1.8. | $i-C_3H_7$ | $i-C_3H_7$ | H | $C_2H_5$ | sec. $C_4H_9$ | Cl | 130 with decomp. |
| 1.1.9. | $CH_3$ | $CH_3$ | H | $CH_3$ | $i-C_3H_7$ | Cl | 92 with decomp. |
| 1.1.10. | $CH_3$ | $CH_3$ | H | $C_2H_5$ | $i-C_3H_7$ | Cl | 88–90 with decomp. |
| 1.1.11. | $C_2H_4$ | $C_2H_5$ | H | $C_2H_5$ | $i-C_2H_7$ | Cl | 126 with decomp. |
| 1.1.12. | cyclopentyl | $i-C_3H_7$ | H | $CH_3$ | $i-C_3H_7$ |  | 166–168 |
| 1.1.13. | cyclopentyl | $i-C_3H_7$ | H | $C_2H_5$ | $i-C_3H_7$ | Cl | 123–124.5 |
| 1.1.14. | cyclopentyl | $C_2H_5$ | H | $C_2H_5$ | $i-C_3H_7$ | Cl | 112–113.5 |
| 1.1.15. | cyclopentyl | $C_2H_5$ | H | $CH_3$ | $i-C_3H_7$ | Cl | 125–127 |
| 1.1.16. | 2-cyclopenten-1-yl | $C_2H_5$ | H | $CH_3$ | $i-C_3H_7$ | Cl | 112–113 |
| 1.1.17. | 2-cyclopenten-1-yl | $i-C_3H_7$ | H | $CH_3$ | $i-C_3H_7$ | Cl | 162–164.5 |
| 1.1.18. | 2-cyclopenten-1-yl | $i-C_3H_7$ | H | $C_2H_5$ | $i-C_3H_7$ | Cl | 127.5–129 |
| 1.1.19. | cyclopentyl | $i-C_3H_7$ | H | $CH_3$ | sec. $C_4H_9$ | Cl | 155–156.5 |
| 1.1.20. | cyclopentyl | $i-C_3H_7$ | H | $C_2H_5$ | sec. $C_4H_9$ | Cl | 124.5–125.5 |
| 1.1.21. | cyclopentyl | $CH_3$ | H | $CH_3$ | $i-C_3H_7$ | Cl | 115.5–117 |
| 1.1.22. | cyclopentyl | $CH_3$ | H | $C_2H_5$ | $i-C_3H_7$ | Cl | 103–104.5 |

1.2. End products 1.2.1.
N-(2,6-diisopropylphenyl)-N-methoxycarbonyl-N'-isopropylisothiourea 15 g of N-(2,6-diisopropylphenyl)-N'-isopropyl-S-methoxycarbonylisothiourea hydrochloride are dis-

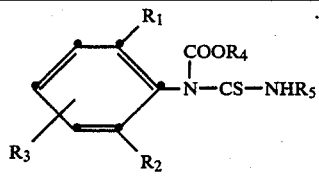

| Comp. No. | $R_1$ | $R_2$ | $R_3$ | $R_4$ | $R_5$ | Physical data |
|---|---|---|---|---|---|---|
| 1.2.2. | $C_2H_5$ | $i-C_3H_7$ | H | $CH_3$ | $i-C_3H_7$ | m.p. 46°–49° C. |
| 1.2.3. | $C_2H_5$ | $i-C_3H_7$ | H | $C_2H_5$ | $i-C_3H_7$ | $n_D^{22}$: 1.5355 |
| 1.2.4. | $i-C_3H_7$ | $i-C_3H_7$ | H | $C_2H_5$ | $i-C_3H_7$ | m.p. 111°–114° C. |
| 1.2.5. | $i-C_3H_7$ | $i-C_3H_7$ | H | $i-C_3H_7$ | | m.p. 85° C. |
| 1.2.6. | cyclo-pentyl | $i-C_3H_7$ | H | $CH_3$ | $i-C_3H_7$ | m.p. 78°–80° C. |
| 1.2.7. | cyclo-pentyl | $i-C_3H_7$ | H | $C_2H_5$ | $i-C_3H_7$ | m.p. 90°–92° C. |
| 1.2.8. | cyclo-pentyl | $C_2H_5$ | H | $CH_3$ | $i-C_3H_7$ | $n_D^{23}$: 1.5540 |
| 1.2.9. | cyclo-pentyl | $C_2H_5$ | H | $C_2H_5$ | $i-C_3H_7$ | $n_D^{23}$: 1.5462 |
| 1.2.10 | 2-cyclo-penten-1-yl | $i-C_3H_7$ | H | $C_2H_5$ | $i-C_3H_7$ | m.p. 81°–83° C. |
| 1.2.11. | 2-cyclo-penten-1-yl | $C_2H_5$ | H | $CH_3$ | $i-C_3H_7$ | $n_D^{25}$: 1.5555 |

Verb Nr.

| Comp. No. | $R_1$ | $R_2$ | $R_3$ | $R_4$ | $R_5$ | Physical data |
|---|---|---|---|---|---|---|
| 1.2.12. | 2-cyclo-penten-1-yl | $C_2H_5$ | H | $C_2H_5$ | $i-C_3H_7$ | $n_D^{25}$: 1.5520 |
| 1.2.13. | 2-cyclo-penten-1-yl | $i-C_3H_7$ | H | $CH_3$ | $i-C_3H_7$ | m.p. 78°–80° C. |
| 1.2.14. | cyclo-pentyl | $i-C_3H_7$ | H | $CH_3$ | sec. $C_4H_9$ | $n_D^{24}$: 1.5440 |
| 1.2.15. | cyclo-pentyl | $i-C_3H_7$ | H | $C_2H_5$ | sec. $C_4H_9$ | $n_D^{24}$: 1.5382 |
| 1.2.16. | cyclo-pentyl | $CH_3$ | H | $CH_3$ | $i-C_3H_7$ | $n_D^{23.5}$: 1.5570 |
| 1.2.17. | cyclo-pentyl | $CH_3$ | H | $C_2H_5$ | $i-C_3H_7$ | $n_D^{24}$: 1.5491 |

EXAMPLE 2: Formulations of active ingredients of the formulae I and IV according to preparation examples 1.1. and 1.2

(%=percent by weight)

| 2.1. Emulsifiable concentrates | (a) | (b) |
|---|---|---|
| active ingredient according to preparation example 1.1 or 1.2. | 10% | 25% |
| Ca dodecylbenzenesulphonate | — | 5% |
| castor oil polyethylene glycol ether (36 mol EO) | 25% | 5% |
| cyclohexanone | — | 40% |
| butanol | 15% | — |
| xylene mixture | — | 25% |
| ethyl acetate | 50% | — |

Emulsions of any desired concentration can be produced from such concentrates by dilution with water.

| 2.2. Solutions | (a) | (b) |
|---|---|---|
| active ingredient according to preparation example 1.1. or 1.2. | 10% | 5% |
| polyethylene glycol (MW 400) | 70% | — |
| N-methyl-2-pyrrolidone | 20% | 20% |
| epoxidised coconut oil | — | 1% |
| petroleum fraction (boiling range 160–190° C.) | — | 74% |

The solutions are suitable for use in the form of very small drops.

| 2.3. Granulates | (a) | (b) |
|---|---|---|
| active ingredient according to preparation example 1.1. or 1.2. | 5% | 10% |
| kaolin | 94% | — |
| highly dispersed silicic acid | 1% | — |
| attapulgite | — | 90% |

The active ingredient is dissolved in methylene chloride and sprayed onto the carrier, and the solvent is then evaporated off in vacuo.

| 2.4. Extruder granulate | |
|---|---|
| active ingredient according to preparation example 1.1. or 1.2. | 10% |

-continued

| 2.4. Extruder granulate | |
| --- | --- |
| Na lignosulphonate | 2% |
| carboxymethylcellulose | 1% |
| kaolin | 87% |

The active ingredient is mixed and ground with the adjuvants and moistened with water. The mixture is extruded and then dried in a stream of air.

| 2.5. Coated granulate | |
| --- | --- |
| active ingredient according to preparation example 1.1. or 1.2. | 3% |
| polyethylene glycol (MW 200) | 3% |
| kaolin | 94% |

The finely ground active ingredient is applied uniformly, in a mixer, to the kaolin, which has been moistened with polyethylene glycol. Dust-free coated granulates are thus obtained.

| 2.6. Dusts | (a) | (b) | (c) | (d) |
| --- | --- | --- | --- | --- |
| active ingredient according to preparation example 1.1. or 1.2. | 2% | 5% | 5% | 8% |
| highly dispersed silicic acid | 1% | 5% | — | — |
| talcum | 97% | — | 95% | — |
| kaolin | — | 90% | — | 92% |

Ready-for-use dusts are obtained by mixing the carriers intimately with the active ingredient and, if appropriate, grinding the mixture in a suitable mill.

| 2.7. Wettable powders | (a) | (b) | (c) |
| --- | --- | --- | --- |
| active ingredient according to preparation example 1.1. or 1.2. | 20% | 50% | 75% |
| Na lignosulphonate | 5% | 5% | — |
| Na lauryl sulphate | 3% | — | 5% |
| Na diisobutylnaphthalene-sulphonate | — | 6% | 10% |
| octylphenolpolyethylene glycol ether (7-8 mol EO) | — | 2% | — |
| highly dispersed silicic acid | 5% | 10% | 10% |
| kaolin | 67% | 27% | — |

The active ingredient is mixed well with the adjuvants and ground in a suitable mill. Wettable powders are obtained that can be diluted with water to form suspensions of any desired concentration.

| 2.8. Suspension concentrate | |
| --- | --- |
| active ingredient according to preparation example 1.1. or 1.2. | 40% |
| ethylene glycol | 10% |
| nonylphenolpolyethylene glycol ether (15 mol EO) | 6% |
| Na lignosulphonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient is intimately mixed with the adjuvants. A suspension concentrate is thus obtained from which suspensions of any desired concentration can be produced by dilution with water.

EXAMPLE 3: BIOLOGICAL TESTS

3.1. Action against Lucilia sericata 1 ml of an aqueous preparation containing 0.5% active ingredient is added at 50° C. to 9 ml of a culture medium. Approximately 30 Lucilia sericata larvae which have just emerged are then added to the culture medium. The insecticidal action is assessed after 48 and 96 hours by determining the mortality.

Compounds according to Examples 1.1. and 1.2. exhibit good action against Lucilia sericata in this test.

3.2 Action against Aëdes aegypti

An amount of a 0.1% acetone solution of the active ingredient sufficient to produce a concentration of 12.5 ppm is pipetted onto the surface of 150 ml of water in a container. After the evaporation of the acetone, 30 to 40 2-day-old Aëdes larvae are placed in the container. The mortality is checked after 2 and 7 days. Compounds according to Examples 1.1. and 1.2. exhibit good action in this test.

3.3. Action as a stomach insecticide against Spodoptera littoralis larvae ($L_1$)

Cotton plants in the cotyledon stage are sprayed with an aqueous active ingredient emulsion (obtained from a 10% emulsifiable concentrate), the active ingredient emulsion containing 400 ppm of the compound to be tested.

When the coating has dried, Spodoptera littoralis larvae in the first larval stage are settled on each cotton plant. The test is carried out at 26° C. and at approximately 50% relative humidity. The mortality is determined after 2 and 3 days, and after 5 days disorders in the development and sloughing of the larvae are evaluated.

Compounds according to Examples 1.1. and 1.2. exhibit good action in this test.

3.4. Action against acarina that damage plants:

Tetranychus urticae (OP-sensitive) and Tetranychus cinnabarinus (OP-tolerant) 16 hours before the start of the test for acaricidal action, an infested piece of leaf from a mass culture of Tetranychus urticae (OP-sens.) or Tetranychus cinnabarinus (OP-tol.) is placed on the primary leaves of Phaseolus vulgaris plants (the tolerance is diazinon tolerance).

The infested plants so treated are sprayed with a test solution containing 400 ppm of the compound to be tested until they are thoroughly wetted. After 24 hours and again after 7 days, imagines and larvae (all mobile stages) are evaluated under a binocular microscope for living and dead individuals. One plant is used per concentration and per test species. During the course of the test, the plants are kept in greenhouse cabins at 25° C.

Compounds according to Examples 1.1. and 1.2. exhibit good action against Tetranychus urticae and Tetranychus cinnabarinus in this test.

3.5. Contact action against Nephotettix cincticeps (nymphs)

The test is carried out on growing plants. Approximately 20-day-old rice plants approximately 15 cm tall are planted in pots (diameter 5.5. cm).

The plants, which are located on a turntable, are each sprayed with 100 ml of an acetone solution containing 400 ppm of the active ingredient to be tested. After the spray coating has dried, 20 nymphs of the test insects in the second or third stage of development are settled on each plant. In order to prevent the cicadas from escaping, a Plexiglass cylinder is placed over each infested plant and covered with a gauze lid. The nymphs are kept on the treated plants, which must be watered again at least once, for 5 days. The test is carried out at a temperature of approximately 23° C., at 55% relative humidity and with an illumination period of 16 hours.

Compounds according to Examples 1.1. and 1.2. exhibit good action in this test.

3.6. Contact action against *Nilaparvata lugens* (nymphs)

The test is carried out on growing plants. Approximately 20-day-old rice plants approximately 15 cm tall are planted in pots (diameter 5.5 cm).

The plants, which are located on a turntable, are each sprayed with 100 ml of an acetone solution containing 400 ppm of the active ingredient to be tested. After the spray coating has dried, 20 nymphs of the test insects in the second or third stage of development are settled on each plant. In order to prevent the cicadas from escaping, a Plexiglass cylinder is placed over each infested plant and covered with a gauze lid. The nymphs are kept on the treated plants, which must be watered again at least once, for 5 days. The test is carried out at a temperature of approximately 23° C., at 55% relative humidity and with an illumination period of 16 hours.

Compounds according to Examples 1.1. and 1.2. exhibit good action in this test.

3.7. Systemic action against *Nilaparvata lugens*

Approximately 10-day-old rice plants (approximately 10 cm tall) and a plastics beaker containing 20 ml of an aqueous emulsion preparation of the active ingredient to be tested in a concentration of 100 ppm are used. The beaker is closed with a plastics lid provided with holes and the roots of the rice plants are pushed through those holes into the aqueous test preparation. The holes are then packed with cotton wool in order to hold the plants in position and eliminate the effect of the gas phase from the test preparation. 20 *Nilaparvata lugens* nymphs in the N2 to N3 stage are then settled on each rice plant, and the plants are each covered with a plastics cylinder. The test is carried out at 20° C. and 60% relative humidity, with an illumination period of 16 hours. After 5 days, the number of dead test insects is estimated in comparison with untreated controls. It is thus determined whether the active ingredient taken up via the roots kills the test insects on the upper parts of the plants.

Compounds according to Examples 1.1. and 1.2. exhibit 80–100% action (mortality) against *Nilaparvata lugens* in the above test.

3.8. Action against soil insects (*Diabrotica balteata*)

150 ml portions of aqueous emulsion preparations containing the active ingredient to be tested in a concentration of 400 ppm are each mixed with 350 ml of soil (consisting of 95% by volume of sand and 5% by volume of peat). Plastics beakers having an upper diameter of approximately 10 cm are then partially filled with the soil so treated. Ten *Diabrotica balteata* larvae in the third larval stage are placed in each beaker together with four corn seedlings, and the beakers are filled to the top with soil. The filled beakers are covered with plastics film and kept at a temperature of approximately 22° C. Ten days after the start of the test, the soil in the beakers is sieved off and the larvae which are left behind are checked for mortality.

Compounds according to Examples 1.1. and 1.2. exhibit good action in the above test.

3.9. Action against ticks in various stages of development

The test objects used are larvae (in each case approximately 50), nymphs (in each case approximately 25) and imagines (in each case approximately 10) of the tick species *Rhipicephalus bursa, Amblyomma hebraeum* and *Boophilus microplus*. The test animals are immersed for a short time in aqueous emulsions of the substances to be tested in a concentration of 400 ppm. The emulsions, which are in test tubes, are then soaked up with cotton wool and the wetted test animals are left in the tubes thus contaminated. The test is evaluated (% mortality) after 3 days in the case of larvae and after 14 days in the case of nymphs and imagines.

Compounds according to Examples 1.1. and 1.2. exhibit good action in the above test.

3.10. Action against *Plasmopara viticola* on vines

Residual protective action

Vine seedlings in the 4–5 leaf stage are sprayed with a spray liquor prepared from a wettable powder of the active ingredient (0.02% active ingredient). After 24 hours, the treated plants are infected with a sporangia suspension of the fungus. After 6 days' incubation at 95–100% relative humidity and 20° C., the fungal attack is assessed.

Compounds according to Examples 1.1. and 1.2. exhibit good action against Plasmopara. For example, compound no. 1.2.13. reduces Plasmopara attack to from 0 to 5%. In contrast, untreated but infected control plants exhibit a Plasmopara attack of 100%.

We claim:

1. A compound of the formula I

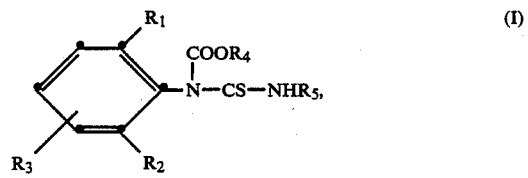

in which $R_1$ and $R_2$ are each $C_1$-$C_{10}$alkyl, $C_3$-$C_7$cycloalkyl or $C_5$-$C_6$cycloalkenyl, $R_3$ is hydrogen, halogen, $C_1$-$C_{10}$alkyl, $C_1$-$C_{10}$alkoxy or $C_1$-$C_{10}$alkylthio, $R_4$ is $C_1$-$C_{10}$alkyl, $C_2$-$C_{10}$alkenyl, $C_2$-$C_{10}$alkynyl or phenyl-$C_1$-$C_7$alkyl; $C_1$-$C_{10}$alkyl, $C_2$-$C_{10}$alkenyl, $C_2$-$C_{10}$alkynyl or phenyl-$C_1$-$C_7$alkyl each substituted one to eleven times by fluorine, chlorine or bromine or interrupted by one oxygen or sulphur atom; $C_3$-$C_8$cycloalkyl; or $C_3$-$C_8$cycloalkyl substituted one to three times by fluorine, chlorine, bromine or by $C_1$-$C_5$alkyl, and $R_5$ is $C_1$-$C_{10}$alkyl; phenyl-$C_1$-$C_7$alkyl; $C_1$-$C_{10}$alkyl or phenyl-$C_1$-$C_7$alkyl each substituted one to eleven times by fluorine, chlorine or bromine or interrupted by one oxygen or sulphur atom; $C_3$-$C_8$cycloalkyl; or $C_3$-$C_8$cycloalkyl substituted one to three times by fluorine, chlorine, bromine or by $C_1$-$C_5$alkyl.

2. A compound of the formula I according to claim 1, in which

R₁ is C₁-C₅alkyl, cyclopentyl or cyclopentenyl,
R₂ is C₁-C₅alkyl,
R₃ is hydrogen, halogen, C₁-C₃alkyl or C₁-C₃alkoxy,
R₄ is C₁-C₅alkyl, C₂-C₅alkenyl or C₂-C₅alkynyl; C₁-C₅alkyl, C₂-C₅alkenyl, C₂-C₅alkynyl or phenyl-C₁-C₅alkyl each substituted one to eleven times by fluorine, chlorine or bromine or interrupted by oxygen or sulphur; or C₃-C₆cycloalkyl, and
R₅ is C₁-C₅alkyl, or C₁-C₅alkyl substituted one to eleven times by fluorine, chlorine or bromine or interrupted by oxygen or sulphur.

3. A compound of the formula I according to claim 2, in which

R₁ is C₁-C₃alkyl or cyclopentyl,
R₂ is C₁-C₃alkyl,
R₃ is hydrogen, and
R₄ and R₅ are C₁-C₄alkyl.

4. A compound according to claim 2 of the formulae

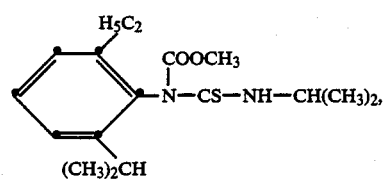

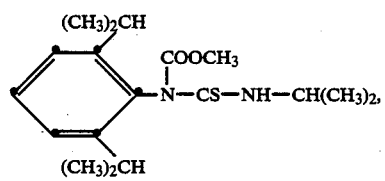

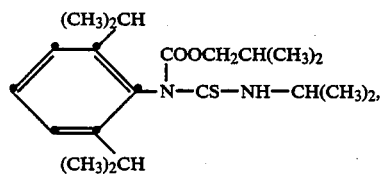

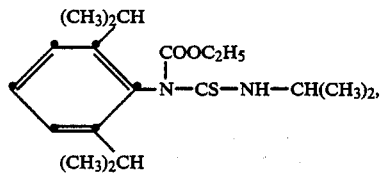

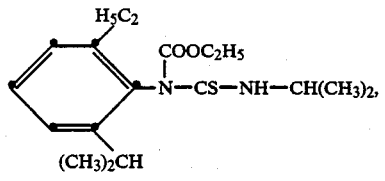

-continued

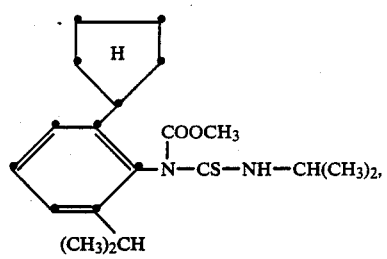

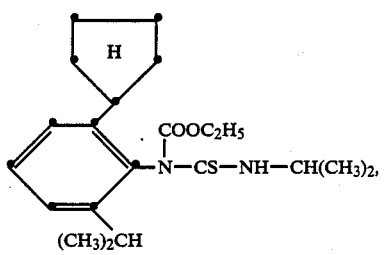

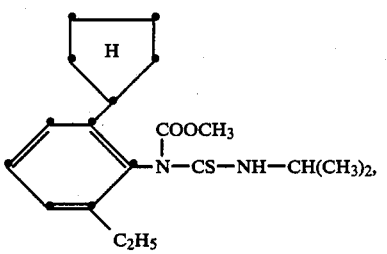

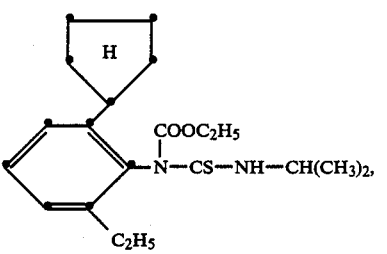

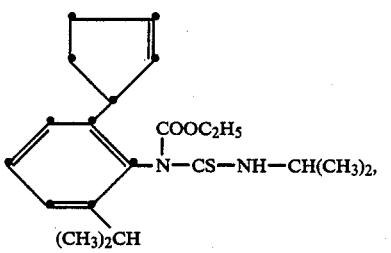

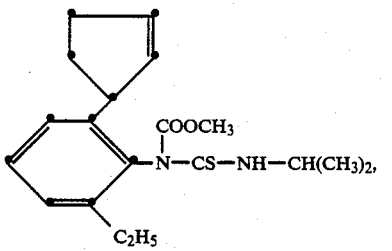

-continued

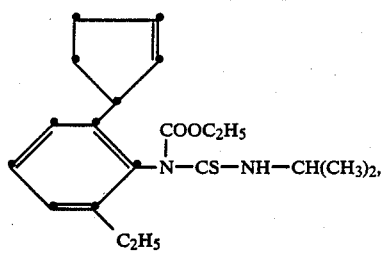

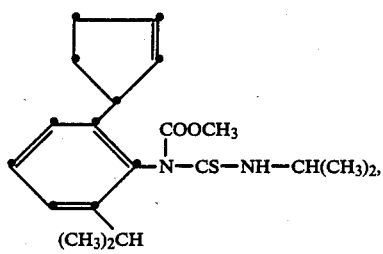

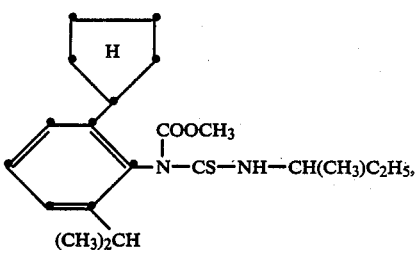

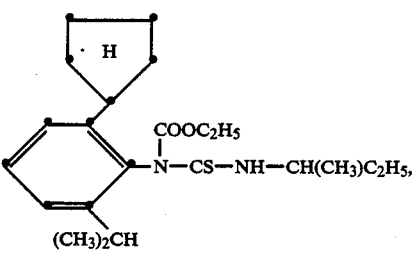

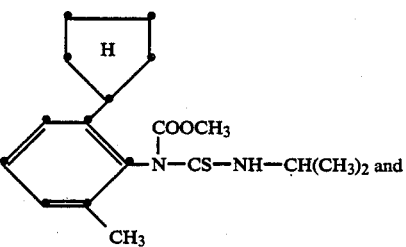

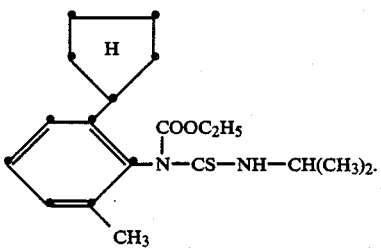

5. A pesticidal composition which contains as active component an insecticidally, arachnicidally or fungicidally effective amount of a compound of the formula I

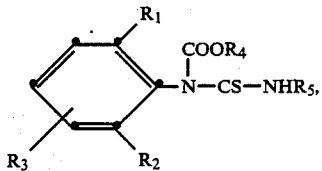

or a compound of the formula IV

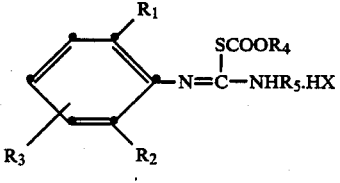

in which
$R_1$ and $R_2$ are each $C_1$-$C_{10}$alkyl, $C_3$-$C_7$cycloalkyl or $C_5$-$C_6$cycloalkenyl,
$R_3$ is hydrogen, halogen, $C_1$-$C_{10}$alkyl, $C_1$-$C_{10}$alkoxy or $C_1$-$C_{10}$alkylthio,
$R_4$ is $C_1$-$C_{10}$alkyl, $C_2$-$C_{10}$alkenyl, $C_2$-$C_{10}$alkynyl or phenyl-$C_1$-$C_7$alkyl; $C_1$-$C_{10}$alkyl, $C_2$-$C_{10}$alkenyl, $C_2$-$C_{10}$alkynyl or phenyl-$C_1$-$C_7$alkyl each substituted one to eleven times by fluorine, chlorine or bromine or interrupted by one oxygen or sulphur atom; $C_3$-$C_8$cycloalkyl; or $C_3$-$C_8$cycloalkyl substituted one to three times by fluorine, chlorine, bromine or by $C_1$-$C_5$alkyl, and
$R_5$ is $C_1$-$C_{10}$alkyl; phenyl-$C_1$-$C_7$alkyl; $C_1$-$C_{10}$alkyl or phenyl-$C_1$-$C_7$alkyl each substituted one to eleven times by fluorine, chlorine or bromine or interrupted by one oxygen or sulphur atom; $C_3$-$C_8$cycloalkyl; or $C_3$-$C_8$cycloalkyl substituted one to three times by fluorine, chlorine, bromine or by $C_1$-$C_5$alkyl, and
X represents the radical of a hydrohalic acid, together with a pesticidally acceptable carrier or other adjuvant.

6. A pesticidal composition according to claim 5, which contains as active compound a compound of the formula I or IV in which
$R_1$ is $C_1$-$C_5$alkyl, cyclopentyl or cyclopentenyl,
$R_2$ is $C_1$-$C_5$alkyl,
$R_3$ is hydrogen, halogen, $C_1$-$C_3$alkyl or $C_1$-$C_3$alkoxy,
$R_4$ is $C_1$-$C_5$alkyl, $C_2$-$C_5$alkenyl or $C_2$-$C_5$alkynyl; $C_1$-$C_5$alkyl, $C_2$-$C_5$alkenyl, $C_2$-$C_5$alkynyl or phenyl-$C_1$-$C_5$alkyl each substituted one to eleven times by fluorine, chlorine or bromine or interrupted by oxygen or sulphur; or $C_3$-$C_6$cycloalkyl, and
$R_5$ is $C_1$-$C_5$alkyl, or $C_1$-$C_5$alkyl substituted one to eleven times by fluorine, chlorine or bromine or interrupted by oxygen or sulphur, and
X is the radical of a hydrohalic acid.

7. A pesticidal composition according to claim 6, which contains as active component at least one compound of the formula I or IV in which
$R_1$ is $C_1$-$C_3$alkyl or cyclopentyl,
$R_2$ is $C_1$-$C_3$alkyl,
$R_3$ is hydrogen, and
$R_4$ and $R_5$ are $C_1$-$C_4$alkyl, and
X is chlorine.

8. A method for controlling pests on animals and plants, characterised in that the pests in their various stages of development are brought into contact with a pesticidally effective amount of a compound of the formula I

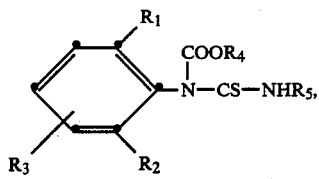

or of the formula IV

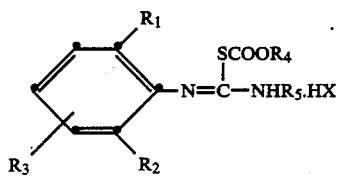

in which $R_1$ and $R_2$ are each $C_1$-$C_{10}$alkyl, $C_3$-$C_7$cycloalkyl or $C_5$-$C_6$cycloalkenyl, $R_3$ is hydrogen, halogen, $C_1$-$C_{10}$alkyl, $C_1$-$C_{10}$alkoxy or $C_1$-$C_{10}$alkylthio, $R_4$ is $C_1$-$C_{10}$alkyl, $C_2$-$C_{10}$alkenyl, $C_2$-$C_{10}$alkynyl or phenyl-$C_1$-$C_7$alkyl; $C_1$-$C_{10}$alkyl, $C_2$-$C_{10}$alkenyl, $C_2$-$C_{10}$alkynyl or phenyl-$C_1$-$C_7$alkyl each substituted one to eleven times by fluorine, chlorine or bromine or interrupted by one oxygen or sulphur atom; $C_3$-$C_8$cycloalkyl; or $C_3$-$C_8$cycloalkyl substituted one to three times by fluorine, chlorine, bromine or by $C_1$-$C_5$alkyl, and $R_5$ is $C_1$-$C_{10}$alkyl; phenyl-$C_1$-$C_7$alkyl; $C_1$-$C_{10}$alkyl or phenyl-$C_1$-$C_7$alkyl each substituted one to eleven times by fluorine, chlorine or bromine or interrupted by one oxygen or sulphur atom; $C_3$-$C_8$cycloalkyl; or $C_3$-$C_8$cycloalkyl substituted one to three times by fluorine, chlorine, bromine or by $C_1$-$C_5$alkyl, and X is the radical of a hydrohalic acid.

9. A method according to claim 8 for controlling insects, arachnids and plant-pathogenic fungi.

* * * * *